(12) United States Patent
Jiang et al.

(10) Patent No.: US 9,371,259 B2
(45) Date of Patent: Jun. 21, 2016

(54) METHOD FOR PREPARING VINYL CHLORIDE FROM ACETYLENE AND DICHLORETHANE

(75) Inventors: Biao Jiang, Shanghai (CN); Jinguang Zhong, Fujian (CN)

(73) Assignees: SHANGHAI ADVANCED RESEARCH INSTITUTE, CHINESE ACADEMY OF SCIENCES, Shanghai (CN); ZHONGKE YIGONG (SHANGHAI) CHEMICAL TECHNOLOGY CO., LTD., Xiamen, Fujian (CN)

( * ) Notice: Subject to any disclaimer, the term of this patent is extended or adjusted under 35 U.S.C. 154(b) by 0 days.

(21) Appl. No.: 14/406,931

(22) PCT Filed: Jul. 12, 2012

(86) PCT No.: PCT/CN2012/078540
§ 371 (c)(1),
(2), (4) Date: Dec. 10, 2014

(87) PCT Pub. No.: WO2013/185400
PCT Pub. Date: Dec. 19, 2013

(65) Prior Publication Data
US 2015/0141713 A1    May 21, 2015

(30) Foreign Application Priority Data

Jun. 11, 2012 (CN) .......................... 2012 1 0191433

(51) Int. Cl.
*C07C 17/07* (2006.01)
*C07C 17/08* (2006.01)
(Continued)

(52) U.S. Cl.
CPC ............... *C07C 17/354* (2013.01); *C07C 17/08* (2013.01); *C07C 17/25* (2013.01); *C07C 17/07* (2013.01); *Y02P 20/582* (2015.11)

(58) Field of Classification Search
CPC ................................ C07C 17/07; C07C 17/25
See application file for complete search history.

(56) References Cited

U.S. PATENT DOCUMENTS 2,681,372 A   6/1954 Trotter
2,779,804 A   1/1957 Braconier et al.
(Continued)

FOREIGN PATENT DOCUMENTS

CN   101817723 A   9/2010
(Continued)

OTHER PUBLICATIONS

CN101817723A (English translation), Sep. 1, 2010, pp. 1-4.*

*Primary Examiner* — Jafar Parsa
*Assistant Examiner* — Medhanit Bahta
(74) *Attorney, Agent, or Firm* — Novick, Kim & Lee, PLLC; Allen Xue

(57) ABSTRACT

Provided is a method for preparing vinyl chloride with acetylene and dichlorethane for large-scale industrial production. Acetylene, dichlorethane vapor and hydrogen chloride gas at a molar ratio of 1:(0.3-1.0):(0-0.20) are mixed; the raw mixed gas is preheated; the preheated raw mixed gas passes through a reactor containing a catalyst and reacts; the resultant mixed gas is cooled to 30-50° C. and pressurized to 0.4-1.0 MPa, and then cooled to ambient temperature, and further frozen to −25-15° C. for liquefaction isolation, and unliquefied gas is recycled and reused; liquefied liquid is sent to a rectifying tower for rectification, and vinyl chloride monomers meeting polymerization requirements are obtained. The present invention has the advantages of eliminating mercury contamination completely, simplifying the reactor structure, recycling hydrogen chloride and acetylene, reducing waterwash process, avoiding mass production of waste acid and improving utilization of chlorine.

11 Claims, 2 Drawing Sheets

(51) Int. Cl.
  *C07C 17/25* (2006.01)
  *C07C 17/354* (2006.01)

(56) References Cited

U.S. PATENT DOCUMENTS

| | | |
|---|---|---|
| 2,830,102 A | 4/1958 | Kobe et al. |
| 2,750,410 A | 6/1986 | Hanszen et al. |
| 2013/0204052 A1 | 8/2013 | Jiang et al. |

FOREIGN PATENT DOCUMENTS

| | | |
|---|---|---|
| CN | 102151578 A | 8/2011 |
| CN | 102151581 A | 8/2011 |
| CN | 102441407 A | 5/2012 |
| CN | 102911007 A | 2/2013 |
| WO | 2013005998 A1 | 5/2013 |
| WO | 2013185400 A1 | 12/2013 |

* cited by examiner

METHOD FOR PREPARING VINYL CHLORIDE FROM ACETYLENE AND DICHLORETHANE

BACKGROUND OF THE PRESENT INVENTION

1. Field of Invention

The present invention relates to a preparation method for vinyl chloride, particularly relates to a method for preparing vinyl chloride with acetylene and dichlorethane.

2. Description of Related Arts

Polyvinyl chloride (PVC) is one of the most popular five kinds of plastic, with its production next only to polyethylene (PE), and ranks second plastics production of the world, with an annual production over 40 million tons.

The earliest synthetic method for polyvinyl chloride is acetylene method, i.e., under the catalysis of mercuric chloride, vinyl chloride is synthesized by the addition of acetylene and hydrogen chloride, and further polyvinyl chloride is polymerized by vinyl chlorides. Since mercuric chloride is adopted as a catalyst in this method, there will be serious mercury pollution problem. After the maturity of process for preparing ethylene by petroleum cracking, ethylene method is used to prepare vinyl chloride abroad, and the preparation process of vinyl chloride by the acetylene method had been basically obsoleted since the early 80s. In china, due to the shortage of ethylene resource and the abundance of calcium carbide resource, the production of PVC is still acetylene method-based. However, as the production of acetylene method keeps increasing, it will face with a huge pressure of environmental pollution. Recently, domestic counterparts have committed to the study of a mercury-free catalyst, and have made some achievements.

A Chinese patent application, application No. 201010149180.1, has provided a new preparation method for vinyl chloride, in which method, by taking barium chloride as a catalyst, vinyl chloride is prepared by a catalytic reforming of acetylene dichloroethane, such that opened up a new approach for mercury-free catalyst.

A Chinese patent application, application No. 201110330158.1 (international patent application No.: PCT/CN2011/081317) has provided a preparation method for a catalyst of vinyl chloride prepared by acetylene dichloroethane, and the performance of the catalyst prepared by such method is greatly improved, and basically meets the requirement of industrial production.

During the preparation of vinyl chloride by the catalytic reforming of acetylene dichloroethane, since the addition reaction of acetylene and hydrogen chloride is an exothermic reaction, and dehydrochlorination of dichloroethane is an endothermic reaction, when coupling the two reactions together, a micro exothermic reaction is formed, and the thermal effect of the reaction is not large, so that the reactor may adopt an adiabatic reactor; by a manner of inter cold shock, the reaction temperature may be controlled within a proper range, such that the reactor structure is greatly simplified.

Meanwhile, during the preparation of vinyl chloride by the catalytic reforming of acetylene dichloroethane, there will be some byproduct of hydrogen chloride. Since hydrogen chloride enables to decrease the starting temperature of the catalytic reforming of acetylene dichloroethane, accelerate the reaction velocity, as well as to inhibit a further increase of the concentration of hydrogen chloride in reaction system, thus after separation and recycling, the byproduct of hydrogen chloride feeds in with the acetylene dichloroethane, thereby greatly reducing the feed temperature, as well as helping to extend the service life of catalyst. Moreover, due to constraints of chemical equilibrium, it is impossible to entirely complete the preparation process of vinyl chloride by the catalytic reforming of acetylene dichloroethane at one time, but generally, with a conversion rate just about 80%, thus a separation and recycling performed on the reactant are needed.

SUMMARY OF THE PRESENT INVENTION

In view of the disadvantages of the prior art, an object of the present invention is to provide a method for preparing vinyl chloride with acetylene and dichlorethane for large-scale industrial production.

In order to achieve the above object and other related objects, the present invention adopts the following technical solution:

A method for preparing vinyl chloride with acetylene and dichlorethane of the present invention, comprises the following steps:
1) acetylene, dichlorethane vapor and hydrogen chloride gas are mixed, and the acetylene, dichlorethane and hydrogen chloride are adjusted with a molar ratio of 1:(0.3-1.0):(0-0.20), to obtain a raw mixed gas;
2) the raw mixed gas is preheated;
3) the preheated raw mixed gas pass through a reactor containing a catalyst to perform reaction;
4) the resultant mixed gas in step 3) is cooled to 30-50° C. and pressurized to 0.4-1.0 MPa, and then cooled to ambient temperature, and further frozen to −25-15° C. for liquefaction isolation, and unliquefied gas is recycled and reused;
5) the liquefied liquid in step 4) is sent to a rectifying tower for rectification, and vinyl chloride monomers meeting polymerization requirements are obtained, i.e., the vinyl chloride of the present invention is obtained.

Preferably, in step 1), the acetylene, dichlorethane and hydrogen chloride are at a molar ratio of 1:(0.3-0.6):(0.05-0.20).

Preferably, in step 2), the preheating temperature is 150-230° C.

Preferably, in step 3), the catalyst adopts an activated carbon-supported barium salt catalyst; preferably, the activated carbon-supported barium salt catalyst usually uses an activated carbon-supported barium chloride; the preparation method for the activated carbon-supported barium chloride of the present invention may refer to the application No. 201110330158.1 of Chinese patent application: a catalyst for preparing vinyl chloride and its preparation method and its use thereof.

Preferably, in step 3), the reactor adopts a multistage cold shock fixed bed reactor; preferably, the multistage cold shock fixed bed reactor adopts a 2-5 stages bed reactor to perform reaction, with an alternate adoption of 1-4 cold shocks intermediately, and a cold shock is adopted between two stages of reaction; preferably, the multistage cold shock fixed bed reactor adopts a 3-4 stages bed reactor to perform reaction, with an alternate adoption of 2-3 cold shocks intermediately, and a cold shock is adopted between two stages of reaction;

Preferably, the cold shock adopts a cold feed gas as a cold shock medium, or the cold shock is performed by a directly injection of liquid dichloroethane; it is preferred to adopt a directly injection of liquid dichloroethane to perform the cold shock, to make the temperature of the reactant gas drop to the level accord with the requirement of inlet temperature.

The cold shock medium adopts a cold feed gas, and the cold feed gas is one of cold acetylene, dichlorethane and hydrogen chloride, or a mixture of several gases thereof.

Preferably, inlet temperatures of the multistage cold shock fixed bed reactor are all 150-230° C., outlet temperatures of the multistage cold shock fixed bed reactor are all 220-280° C., by which the conversion ratio of the raw material (refer to acetylene) is up to more than 70%, and even up to more than 80%. The inlet temperatures of each stage of bed reactor may be any value within 150-230° C., while the outlet temperatures of each stage of bed reactor may be any value within 220-280° C., the inlet temperatures of each stage of the bed reactor may be different, and outlet temperatures also may be different, the temperatures may be adjusted according to actual requirements.

Preferably, inlet velocity of the raw mixed gas can be controlled as per cubic meter of catalyst treating 10-100 cubic meter of raw mixed gas per hour; pressure of the reaction can be 0-0.12 MPa (gage pressure), which pressure is the displayed number of the gauge, and 0 MPa represents no pressure, i.e., atmospheric pressure. The reaction pressure of each stage of reactor may be any value within 0-0.12 MPa, the reaction pressure of each stage of reactor may be different and may be adjusted according to actual requirements.

Compared to the existing process of acetylene method, the present invention has the following outstanding advantages:
1) By adopting an activated carbon-supported barium salt catalyst, the mercury contamination is completely eliminated.
2) Since a multistage cold shock reactor is adopted to replace a fixed bed tubular reactor, on one hand, reaction heat can be efficiently utilized; on the other hand, the reactor structure can be greatly simplified, thus advantages are provided for equipment enlargement.
3) Compression refrigeration method is adopted to separate VCM (vinyl chloride), to recycle hydrogen chloride and acetylene, reduce waterwash process, avoid mass production of waste acid and improve utilization of chlorine, as well as to reduce the environmental pollution.

BRIEF DESCRIPTION OF THE DRAWINGS

In FIG. 1, each label is: 1 first stage reactor
2 first stage cold shock device
3 second stage reactor
4 second stage cold shock device
5 third stage reactor
6 catalyst
7 inlet of feed gas
8 inlet of cold shock medium
9 inlet of cold shock medium
10 catalyst
11 catalyst
12 outlet of product gas

In FIG. 2, each label is: 13 inlet of feed gas
14 catalyst
15 inlet of cold shock medium
16 inlet of cold shock medium
17 outlet of product gas
18 first reaction stage
19 first cold shock device
20 second reaction stage
21 second cold shock device
22 third reaction stage

DETAILED DESCRIPTION OF THE PREFERRED EMBODIMENTS

Figure 1:
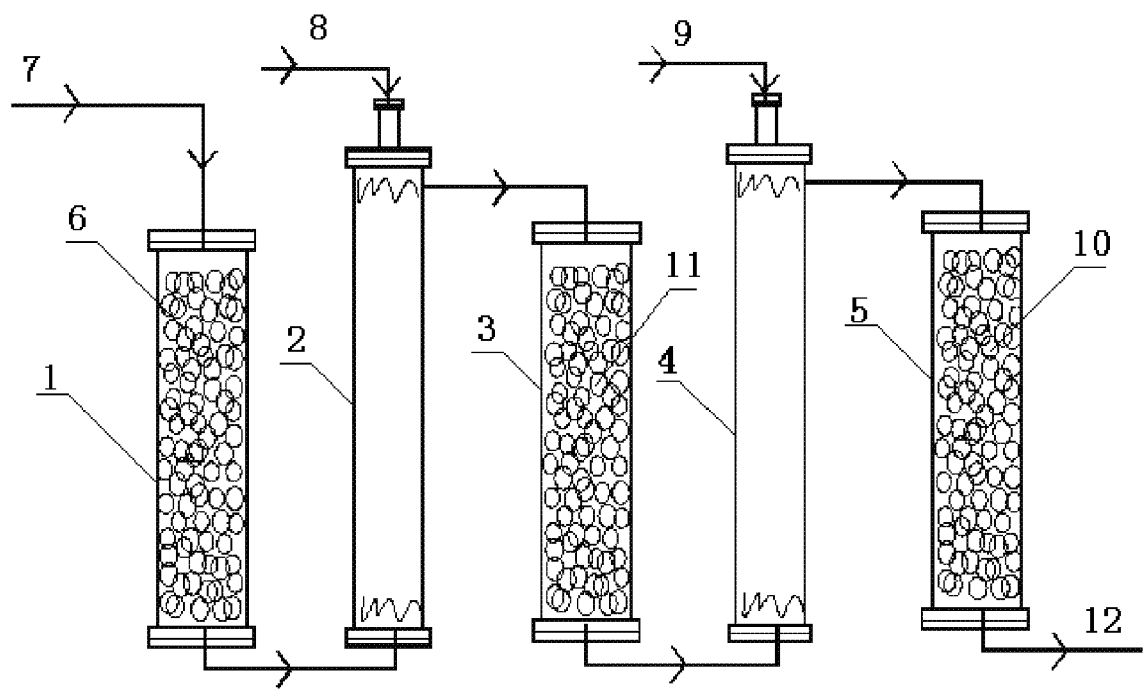
FIG. 1 is a structural diagram of a multistage cold shock fixed bed reactor of a two times cold shock and three stages reaction of an embodiment of the present invention.

The embodiment modes of the present invention are described hereunder through specific examples, and persons skilled in the art may easily understand other advantages and efficacies of the present invention from the contents disclosed in the present description. The present invention may be further implemented or applied through other different specific embodiment modes, and various modifications or amendments may also be made to each of the details in the present description based on different perspectives and applications without departing from the spirit of the present invention.

Embodiment 1

1) Acetylene, dichlorethane vapor and hydrogen chloride gas are mixed, and the acetylene, dichlorethane and hydrogen chloride are adjusted with a molar ratio of 1:0.3:0.2, to obtain a raw mixed gas;
2) The raw mixed gas is preheated to 150° C.;
3) The preheated raw mixed gas pass through a reactor containing a catalyst, the catalyst used is activated carbon-supported barium chloride. The reactor adopts a multistage cold shock fixed bed reactor, and adopts a 2-stage reaction, with a cold shock intermediately. The cold shock is performed by a directly injection manner of liquid dichloroethane, to make the temperature of the reactant gas drop to the level accord with the requirement of inlet temperature. The inlet temperature of the bed reactor is controlled to be 150° C., and the outlet temperature is 280° C., to make the conversion ratio of the raw material (in acetylene terms) is up to 80%. Inlet velocity of the raw mixed gas is controlled as per cubic meter of catalyst treating 100 cubic meter of raw mixed gas per hour; pressure of the reaction is controlled as 0.12 MPa (gage pressure).
4) The resultant mixed gas in step 3) is cooled to 50° C. and pressurized to 1.0 MPa, and then cooled to ambient temperature, and further frozen to 15° C. for liquefaction isolation, and unliquefied gas is recycled and reused;
5) The liquefied liquid in step 4) is sent to a rectifying tower for rectification, and vinyl chloride monomers meeting polymerization requirements are obtained.

Embodiment 2

1) Acetylene, dichlorethane vapor are mixed, and the acetylene, dichlorethane are adjusted with a molar ratio of 1:1, to obtain a raw mixed gas;
2) The raw mixed gas is preheated to 230° C.;
3) the preheated raw mixed gas pass through a reactor containing a catalyst, the catalyst used is activated carbon-supported barium chloride. The reactor adopts a multistage cold shock fixed bed reactor, and adopts a 5 stages reaction, with 4 cold shocks intermediately. The cold shock is performed by cold raw material gas, to make the temperature of the reactant gas drop to the level accord with the requirement of inlet temperature. The inlet temperature of the bed reactor is controlled to be 230° C., and the outlet temperature is 270° C., to make the conversion ratio of the raw material (in acetylene terms) is up to 85%. Inlet velocity of the raw mixed gas is controlled as per cubic meter of catalyst treating 50 cubic meter of raw mixed gas per hour; pressure of the reaction is controlled as 0.10 MPa (gage pressure).

4) The resultant mixed gas in step 3) is cooled to 30° C. and pressurized to 0.4 MPa, and then cooled to ambient temperature, and further frozen to −25° C. for liquefaction isolation, and unliquefied gas is recycled and reused;

5) The liquefied liquid in step 4) is sent to a rectifying tower for rectification, and vinyl chloride monomers meeting polymerization requirements are obtained.

Embodiment 3

Figure 2:
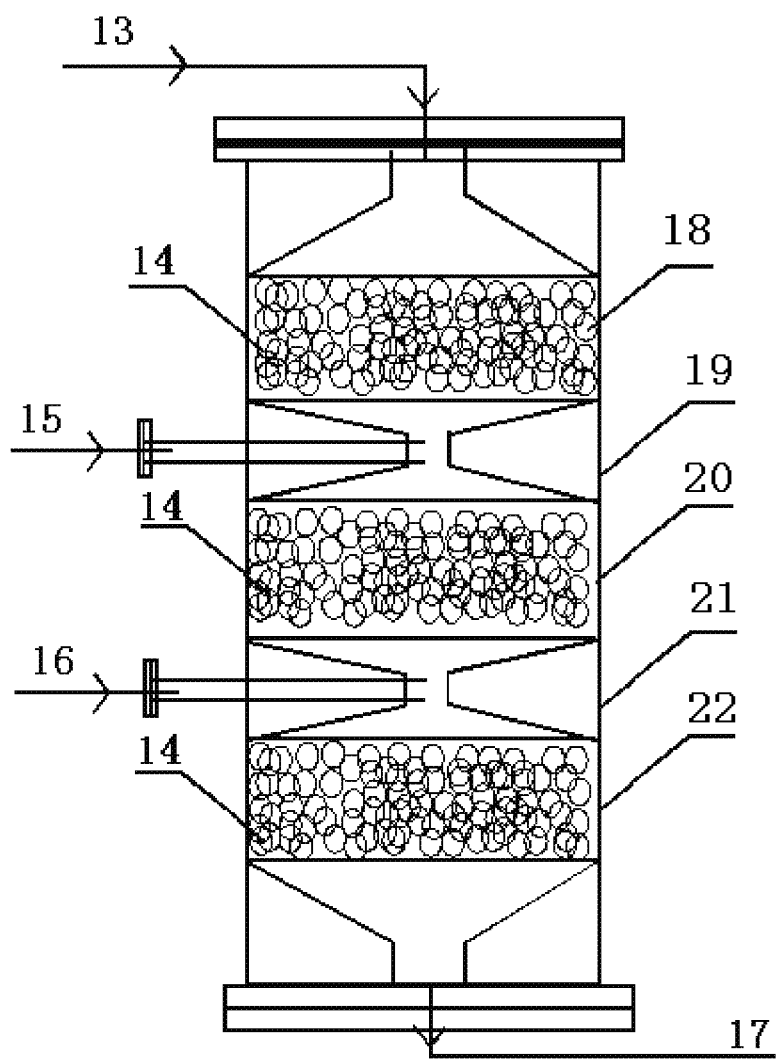
FIG. 2 is a structural diagram of a multistage cold shock fixed bed reactor having a integration of multistage reactions of an embodiment of the present invention.

1) Acetylene, dichlorethane vapor and hydrogen chloride gas are mixed, and the acetylene, dichlorethane and hydrogen chloride are adjusted with a molar ratio of 1:0.5:0.1, to obtain a raw mixed gas;

2) The raw mixed gas is preheated to 160° C.;

3) The preheated raw mixed gas pass through a reactor containing a catalyst, the catalyst used is activated carbon-supported barium chloride. The reactor adopts a multistage cold shock fixed bed reactor, and adopts a 3-stage reaction, with 2 cold shocks intermediately (referring to the multistage cold shock fixed bed reactor of a two times cold shock and three stages reaction as shown in FIG. 1, or the multistage cold shock fixed bed reactor having a integration of multistage reactions as shown in FIG. 2). The cold shock is performed by a directly injection manner of liquid dichloroethane, to make the temperature of the reactant gas drop to the level accord with the requirement of inlet temperature. The inlet temperature of the bed reactor is controlled to be 160° C., and the outlet temperature is 250° C., to make the conversion ratio of the raw material (in acetylene terms) is up to 70%. Inlet velocity of the raw mixed gas is controlled as per cubic meter of catalyst treating 70 cubic meter of raw mixed gas per hour; pressure of the reaction is controlled as 0.08 MPa (gage pressure).

4) The resultant mixed gas in step 3) is cooled to 40° C. and pressurized to 0.6 MPa, and then cooled to ambient temperature, and further frozen to 0° C. for liquefaction isolation, and unliquefied gas is recycled and reused;

5) The liquefied liquid in step 4) is sent to a rectifying tower for rectification, and vinyl chloride monomers meeting polymerization requirements are obtained.

The multistage cold shock fixed bed reactor of a two times cold shock and three stages reaction (as shown in FIG. 1), includes sequentially connected a first stage reactor 1, a first stage cold shock device 2, a second stage reactor 3, a second stage cold shock device 4 and a third stage reactor 5, the first stage reactor 1 is provided with an inlet of raw material gas 7, a top of the first stage cold shock device is provided with an inlet of cold shock medium 8, a top of the second stage cold shock device 4 is provided with an inlet of cold shock medium 9, a bottom of the first stage reactor 1 is connected with a bottom of the first stage cold shock device 2 through a pipe, a top of the first stage cold shock device 2 is connected with a top of the second stage reactor 3 through a pipe, a bottom of the second stage reactor 3 is connected with a bottom of the second stage cold shock device 4 through a pipe, the top of the second stage cold shock device 4 is further connected with a top of the third stage reactor 5 through a pipe, a bottom of the third stage reactor 5 is provided with an outlet of product gas 12, the first stage reactor 1 is filled with a catalyst 6, the second stage reactor 3 is filled with a catalyst 11, the third stage reactor 5 is filled with a catalyst 10.

With regard to the multistage cold shock fixed bed reactor having a integration of multistage reactions (as shown in FIG. 2), a top of the multistage cold shock fixed bed reactor is provided with an inlet of raw material gas 13, and a bottom thereof is provided with an outlet of product gas 17, the multistage cold shock fixed bed reactor having a integration of multistage reactions includes sequentially a first reaction stage 18 (or named as a first stage of reactor 18), a first cold shock device 19 being in communication with the first stage reaction 18, a second reaction stage 20 (or named as a second stage of reactor 20) being in communication with the first cold shock device 19, a second cold shock device 21 being in communication with the second stage reaction 20, and a third reaction stage 22 (or named as a third stage of reactor 22) being in communication with the second cold shock device 21 from top to bottom; all the first stage reaction 18, the second stage reaction 20 and the third stage reaction 22 are filled with a catalyst 14, one side of the first cold shock device 19 is provided with an inlet of cold shock medium 15, and one side of the second cold shock device 21 is provided with an inlet of cold shock medium 16.

Embodiment 4

1) Acetylene, dichlorethane vapor and hydrogen chloride gas are mixed, and the acetylene, dichlorethane and hydrogen chloride are adjusted with a molar ratio of 1:0.6:0.05, to obtain a raw mixed gas;

2) The raw mixed gas is preheated to 170° C.;

3) The preheated raw mixed gas pass through a reactor containing a catalyst, the catalyst used is activated carbon-supported barium chloride. The reactor adopts a multistage cold shock fixed bed reactor, and adopts a 3-stage reaction, with 2 cold shocks intermediately. The cold shock is performed by a directly injection manner of liquid dichloroethane, to make the temperature of the reactant gas drop to the level accord with the requirement of inlet temperature. The inlet temperature of the bed reactor is controlled to be 170° C., and the outlet temperature is 240° C., to make the conversion ratio of the raw material (in acetylene terms) is up to 75%. Inlet velocity of the raw mixed gas is controlled as per cubic meter of catalyst treating 40 cubic meter of raw mixed gas per hour; pressure of the reaction is controlled as 0.05 MPa (gage pressure).

4) The resultant mixed gas in step 3) is cooled to 35° C. and pressurized to 0.7 MPa, and then cooled to ambient temperature, and further frozen to 5° C. for liquefaction isolation, and unliquefied gas is recycled and reused;

5) The liquefied liquid in step 4) is sent to a rectifying tower for rectification, and vinyl chloride monomers meeting polymerization requirements are obtained.

Embodiment 5

1) Acetylene, dichlorethane vapor and hydrogen chloride gas are mixed, and the acetylene, dichlorethane and hydrogen chloride are adjusted with a molar ratio of 1:0.4:0.12, to obtain a raw mixed gas;

2) The raw mixed gas is preheated to 180° C.;

3) The preheated raw mixed gas pass through a reactor containing a catalyst, the catalyst used is activated carbon-supported barium chloride. The reactor adopts a multistage cold shock fixed bed reactor, and adopts a 4-stage reaction, with 3 cold shocks intermediately. The cold shock is performed by a directly injection manner of liquid dichloroethane, to make the temperature of the reactant gas drop to the level accord with the requirement of inlet temperature. The inlet temperature of the bed reactor is controlled to be 180° C., and the outlet temperature is 230° C., to make the conversion ratio of the raw material (in acetylene terms) is up to 70%. Inlet velocity of the raw mixed gas is controlled as per cubic meter of catalyst treating 40 cubic meter of raw mixed gas per hour; pressure of the reaction is controlled as 0.02 MPa (gage pressure).
4) The resultant mixed gas in step 3) is cooled to 50° C. and pressurized to 0.6 MPa, and then cooled to ambient temperature, and further frozen to 10° C. for liquefaction isolation, and unliquefied gas is recycled and reused;
5) The liquefied liquid in step 4) is sent to a rectifying tower for rectification, and vinyl chloride monomers meeting polymerization requirements are obtained.

Embodiment 6

1) Acetylene, dichlorethane vapor and hydrogen chloride gas are mixed, and the acetylene, dichlorethane and hydrogen chloride are adjusted with a molar ratio of 1:0.3:0.15, to obtain a raw mixed gas;
2) The raw mixed gas is preheated to 165° C.;
3) The preheated raw mixed gas pass through a reactor containing a catalyst, the catalyst used is activated carbon-supported barium chloride. The reactor adopts a multistage cold shock fixed bed reactor, and adopts a 3-stage reaction, with 2 cold shock intermediately. The cold shock is performed by a directly injection manner of liquid dichloroethane, to make the temperature of the reactant gas drop to the level accord with the requirement of inlet temperature. The inlet temperature of the bed reactor is controlled to be 165° C., and the outlet temperature is 220° C., to make the conversion ratio of the raw material (in acetylene terms) is up to 75%. Inlet velocity of the raw mixed gas is controlled as per cubic meter of catalyst treating 10 cubic meter of raw mixed gas per hour; pressure of the reaction is controlled as atmospheric pressure.
4) The resultant mixed gas in step 3) is cooled to 30° C. and pressurized to 0.6 MPa, and then cooled to ambient temperature, and further frozen to −5° C. for liquefaction isolation, and unliquefied gas is recycled and reused;
5) The liquefied liquid in step 4) is sent to a rectifying tower for rectification, and vinyl chloride monomers meeting polymerization requirements are obtained.

Embodiment 7

1) Acetylene, dichlorethane vapor are mixed, and the acetylene, dichlorethane are adjusted with a molar ratio of 1:0.3, to obtain a raw mixed gas;
2) The raw mixed gas is preheated to 230° C.;
3) The preheated raw mixed gas pass through a reactor containing a catalyst, the catalyst used is activated carbon-supported barium chloride. The reactor adopts a multistage cold shock fixed bed reactor, and adopts a 5-stage reaction, with 4 cold shock intermediately. The cold shock is performed by a directly injection manner of liquid dichloroethane, to make the temperature of the reactant gas drop to the level accord with the requirement of inlet temperature. The inlet temperature of the bed reactor is controlled to be 230° C., and the outlet temperature is 270° C., to make the conversion ratio of the raw material (in acetylene terms) is up to 85%. Inlet velocity of the raw mixed gas is controlled as per cubic meter of catalyst treating 50 cubic meter of raw mixed gas per hour; pressure of the reaction is controlled as 0.10 MPa (gage pressure).
4) The resultant mixed gas in step 3) is cooled to 30° C. and pressurized to 0.4 MPa, and then cooled to ambient temperature, and further frozen to −25° C. for liquefaction isolation, and unliquefied gas is recycled and reused;
5) The liquefied liquid in step 4) is sent to a rectifying tower for rectification, and vinyl chloride monomers meeting polymerization requirements are obtained.

Embodiment 8

1) Acetylene, dichlorethane vapor and hydrogen chloride gas are mixed, and the acetylene, dichlorethane and hydrogen chloride are adjusted with a molar ratio of 1:1.0:0.12, to obtain a raw mixed gas;
2) The raw mixed gas is preheated to 180° C.;
The preheated raw mixed gas pass through a reactor containing a catalyst, the catalyst used is activated carbon-supported barium chloride. The reactor adopts a multistage cold shock fixed bed reactor, and adopts a 4 stages reaction, with 3 cold shocks intermediately. The cold shock is performed by cold raw material gas, to make the temperature of the reactant gas drop to the level accord with the requirement of inlet temperature. The inlet temperature of the bed reactor is controlled to be 180° C., and the outlet temperature is 230° C., to make the conversion ratio of the raw material (in acetylene terms) is up to 80%. Inlet velocity of the raw mixed gas is controlled as per cubic meter of catalyst treating 40 cubic meter of raw mixed gas per hour; pressure of the reaction is controlled as 0.02 MPa (gage pressure).
4) The resultant mixed gas in step 3) is cooled to 50° C. and pressurized to 0.6 MPa, and then cooled to ambient temperature, and further frozen to 10° C. for liquefaction isolation, and unliquefied gas is recycled and reused;
5) The liquefied liquid in step 4) is sent to a rectifying tower for rectification, and vinyl chloride monomers meeting polymerization requirements are obtained.

The above are preferred embodiments of the present invention, rather than being used to formally or essentially limit the invention; it should be pointed out that, with regard to those skilled in the art, on the premise without departing from the method of the invention, several amendments and supplements may be made, while shall still be covered by the scope of the present invention. All amendments, modifications or equivalent evolutions accomplished by technical solution above revealed and by persons having common knowledge in the technical field without departing from the spirit and scope of the invention shall be considered as equivalent embodiments of the present invention; meanwhile, Any equivalent amendments, modifications and evolutions accomplished by essential technical solutions of the invention, shall still be covered by the scope of the technical solutions of the present invention.

What is claimed is:
1. A method for preparing vinyl chloride, comprising:
1) mixing acetylene, dichlorethane vapor and optionally hydrogen chloride gas to obtain a raw mixed gas, wherein the raw mixed gas has a molar ratio of acetylene:dichlorethane:hydrogen chloride gas at 1:(0.3-1.0):(0-0.20);
2) preheating the raw mixed gas to a preheating temperature to obtain a preheated raw mixed gas;
3) feeding the preheated raw mixed gas into a reactor containing a catalyst;
4) cooling an effluent gas from the reactor to 30-50° C., pressurizing the effluent gas to 0.4-1.0 MPa, and cooling the pressurized effluent gas to ambient temperature, and further cooling the pressurized effluent gas from ambient temperature to −25-15° C. to obtain a liquid; and
5) feeding the liquid to a rectifying tower for rectification, and obtaining vinyl chloride from the rectifying tower.

2. The method according to claim 1, wherein, in step 2), the preheating temperature is 150-230° C.

3. The method according to claim 1, wherein, in step 3), the catalyst is an activated carbon-supported barium salt catalyst.

4. The method according to claim 3, wherein the activated carbon-supported barium salt catalyst is an activated carbon-supported barium chloride.

5. The method according to claim 1, wherein, in step 3), the reactor is a multistage cold shock fixed bed reactor.

6. The method according to claim 5, wherein the multistage cold shock fixed bed reactor comprises 2-5 reaction stages a cold shock between two consecutive reaction stages.

7. The method according to claim 6, wherein the cold shock is accomplished by heat removal using a cold shock medium or by directly injecting liquid dichloroethane into a reaction gas between two consecutive reaction stages.

8. The method according to claim 7, wherein the cold shock medium is the raw mixed gas.

9. The method according to claim 5, wherein the multistage cold shock fixed bed reactor has an inlet temperature in a range of 150-230° C. and an outlet temperature of 220-280° C.

10. The method according to claim 8, wherein a flow rate of the raw mixed gas into the multistage cold shock fixed bed reactor is 10-100 cubic meter of the raw mixed gas per hour.

11. The method according to claim 6, wherein a pressure in the multistage cold shock fixed bead reactor is 0-0.12 MPa (gage pressure).

\* \* \* \* \*